US00PP33255P2

(12) United States Plant Patent
Ritchie et al.

(10) Patent No.: US PP33,255 P2
(45) Date of Patent: Jul. 13, 2021

(54) ***PITTOSPORUM* PLANT NAMED 'PTG19'**

(50) Latin Name: *Pittosporum tenuifolium*
Varietal Denomination: PTG19

(71) Applicants: Jack Ritchie, Central Hawkes Bay (NZ); Kathy Ritchie, Central Hawkes Bay (NZ)

(72) Inventors: Jack Ritchie, Central Hawkes Bay (NZ); Kathy Ritchie, Central Hawkes Bay (NZ)

( * ) Notice: Subject to any disclaimer, the term of this patent is extended or adjusted under 35 U.S.C. 154(b) by 0 days.

(21) Appl. No.: 16/873,830

(22) Filed: Jul. 18, 2020

(51) Int. Cl.
*A01H 5/00* (2018.01)
*A01H 6/00* (2018.01)

(52) U.S. Cl.
USPC ..... Plt./234

(58) Field of Classification Search
USPC ..... Plt./234
CPC ... A01H 5/12; A01H 5/00; A01H 5/02; A01H 6/00
See application file for complete search history.

(56) References Cited

PUBLICATIONS

RHS Plant Finder, retrieved on Jan. 11, 2021, retrieved from the Internet at https://www.rhs.org.uk/Plants/384901/i-Pittosporum-tenuifolium-i-Irish-Luck/Details, one page. (Year: 2021).*
Upov Pluto Plant Variety Database Jan. 8, 2021, retrieved on Jan. 11, 2021, retrieved from the Internet at https://www.upov.int/pluto/en/index.jsp, one page. (Year: 2021).*

* cited by examiner

*Primary Examiner* — June Hwu

(57) ABSTRACT

A new cultivar of *Pittosporum* plant named 'PTG19' that is characterized by glossy green leaves with light silver margins, short internodes, a fast growth rate, a small overall size, a compact habit and good drought tolerance.

2 Drawing Sheets

Botanical classification: *Pittosporum tenuifolium.*
Variety denomination: 'PTG19'.

BACKGROUND OF THE INVENTION

The present invention relates to a new and distinct cultivar of *Pittosporum* plant botanically known as *Pittosporum tenuifolium* and hereinafter referred to by the cultivar name 'PTG19'.

'PTG19' was discovered as a naturally occurring whole plant mutation of *Pittosporum tenuifolium* 'Irish Luck' (not patented) in 2014. The new cultivar was discovered as a single plant in a population of *Pittosporum* 'Irish Luck' plants in a cultivated area of Hawkes Bay, New Zealand. The new cultivar was discovered in a commercial plant nursery container field.

Asexual reproduction of the new cultivar 'PTG19' first occurred by semi-hardwood cuttings in 2014 in Hawkes Bay, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pittosporum* cultivar 'PTG19'. These traits in combination distinguish 'PTG19' as a new and distinct cultivar apart from other existing varieties of *Pittosporum* known by the inventor.

1. *Pittosporum* 'PTG19' exhibits glossy green leaves with light silver margins.
2. *Pittosporum* 'PTG19' exhibits short internodes.
3. *Pittosporum* 'PTG19' exhibits a fast growth rate.
4. *Pittosporum* 'PTG19' exhibits a small overall size and a compact habit.
5. *Pittosporum* 'PTG19' exhibits good drought tolerance.

The closest comparison cultivars are *Pittosporum* 'Stephen's Island' (not patented) and the parent plant *Pittosporum* 'Irish Luck'. 'PTG19' is distinguishable from 'Stephen's Island' by the following characteristics:

1. *Pittosporum* 'PTG19' exhibits green leaves with light silver margins. In comparison, the leaves of 'Stephen's Island' are matte green with darker silver margins.
2. *Pittosporum* 'PTG19' exhibits short internodes. In comparison, the internodes of 'Stephen's Island' are longer.
3. *Pittosporum* 'PTG19' exhibits a fast growth rate. In comparison, the growth rate of 'Stephen's Island' is slower.
4. *Pittosporum* 'PTG19' exhibits a small overall size and a compact habit. In comparison, 'Stephen's Island' has a larger overall size and a more open habit.

'PTG19' is distinguishable from the parent plant 'Irish Luck' by the following characteristics:

1. *Pittosporum* 'PTG19' exhibits a smaller overall size than the overall size of 'Irish Luck'.
2. *Pittosporum* 'PTG19' exhibits a compact habit. In comparison, 'Irish Luck' has a more open habit.

BRIEF DESCRIPTION OF THE DRAWING

The accompanying photographs illustrate the distinguishing traits of *Pittosporum* 'PTG19'.

The photograph of FIG. 1 shows an overall view of a 6 year old plant.

Figure 1:
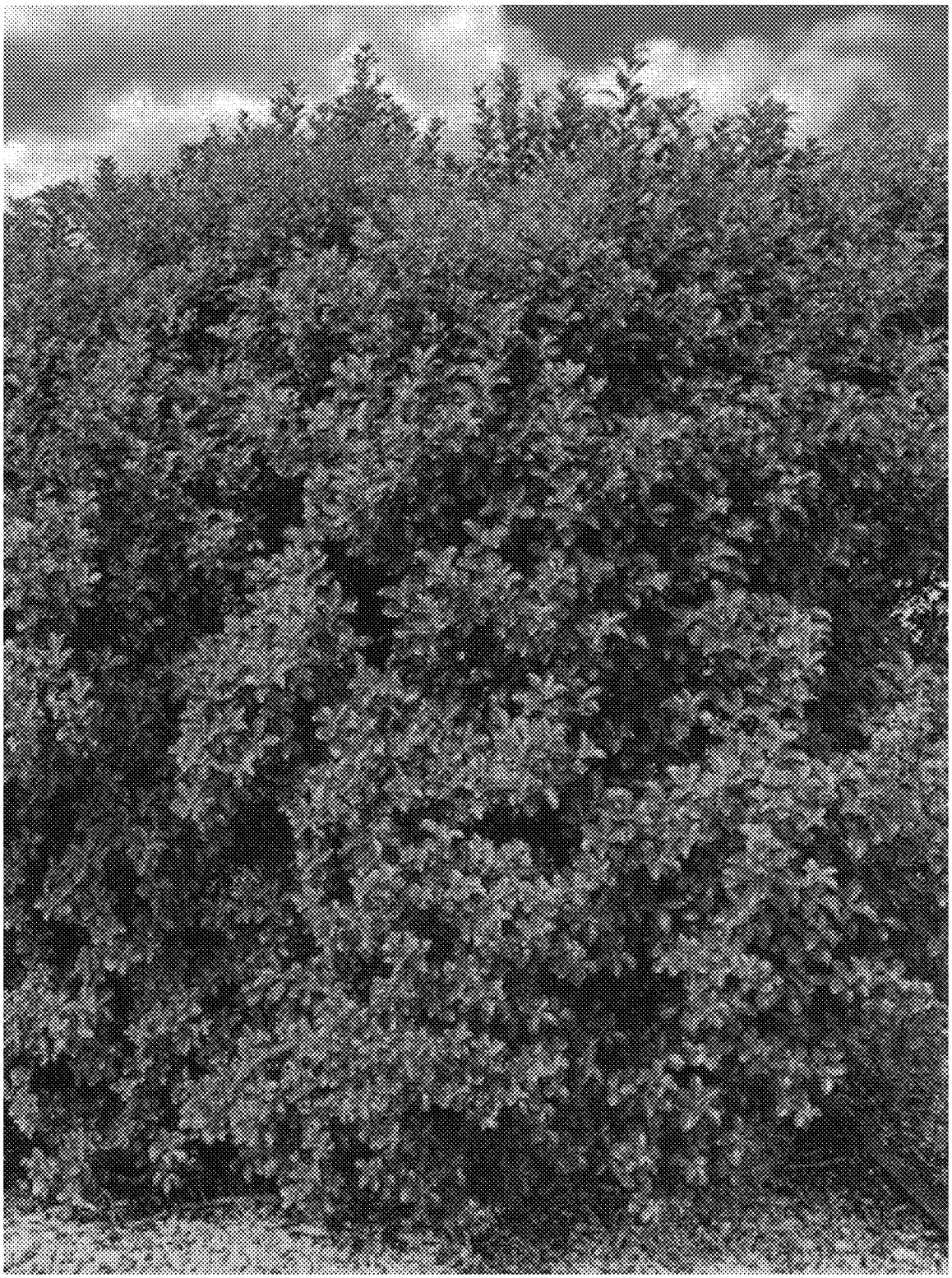
Figure 2:
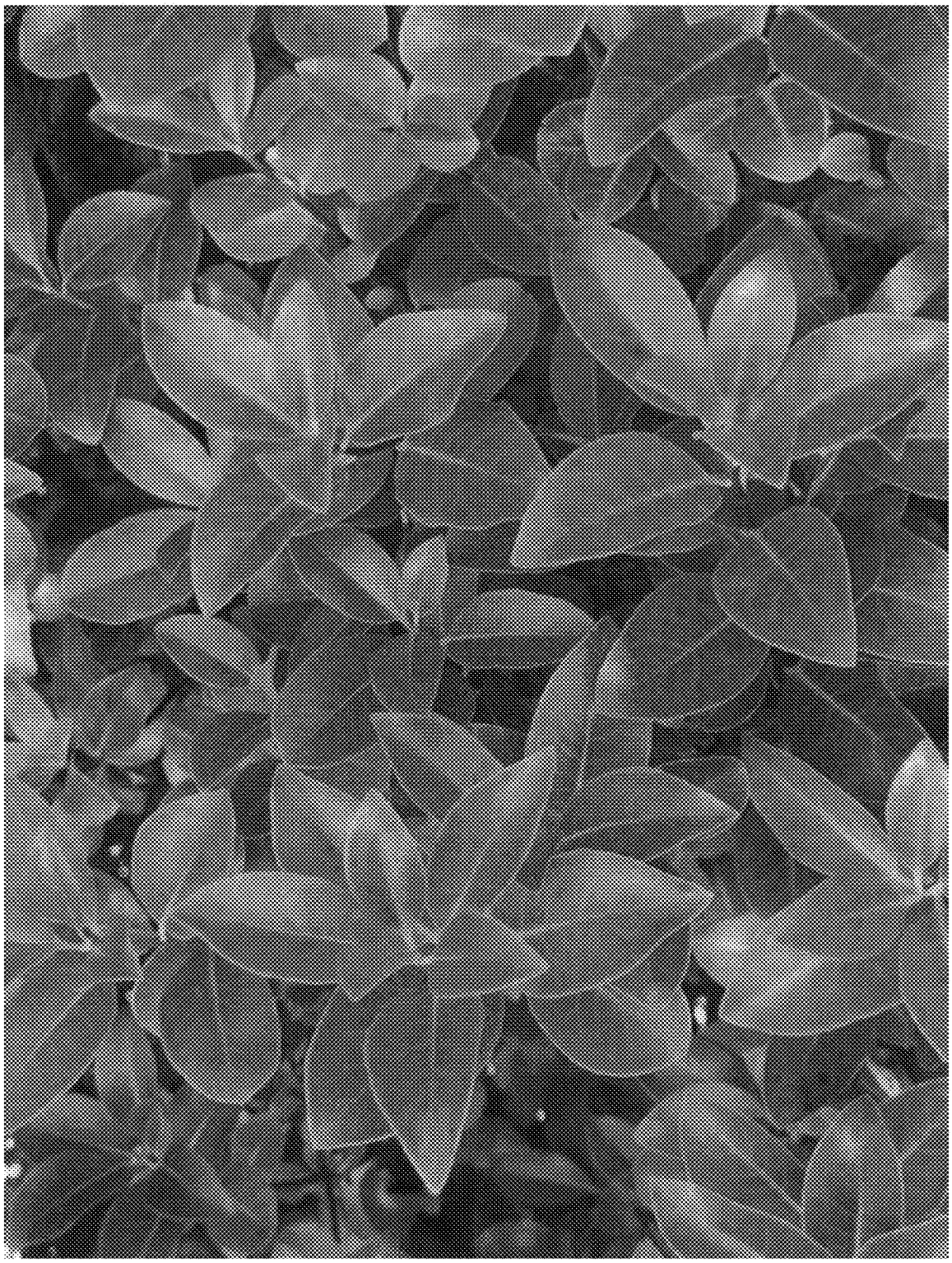

The photograph in FIG. 2 shows a close-up view of the foliage.

The photographs were taken using conventional techniques and although colors may appear different from actual colors due to light reflectance, it is as accurate as possible by conventional photographic techniques.

BOTANICAL DESCRIPTION OF THE PLANT

The following is a detailed description of the new *Pittosporum* cultivar named 'PTG19'. Data was collected in Auckland, New Zealand from 6 year old outdoor field grown plants. The time of year was August and the average temperature was 14 degrees Centigrade during the day and 8 degrees Centigrade at night. The light level was natural light level. Color determinations are in accordance with The Royal Horticultural Society Colour Chart 2015 edition, except where general color terms of ordinary dictionary significance are used. The growing requirements are similar to the species. 'PTG19' has not been tested under all possible conditions and phenotypic differences may be observed with variations in environmental, climatic, and cultural conditions, however, without any variance in genotype.

Botanical classification: *Pittosporum tenuifolium* 'PTG19'.

Parentage: 'PTG19' is a naturally occurring whole plant mutation of *Pittosporum* 'Irish Luck'.

Annual or perennial: Perennial.

Plant type: Evergreen shrub.

Growth habit: Upright, dense.

Plant shape: Oval shaped.

Suitable container size: 2 liter pots.

Plant height to top of foliage: Average 2.5 m.

Plant width: Average 1.8 m.

Vigor: Moderate to high.

Growth rate: Average 30 cm. per year.

Low temperature tolerance: −12° Centigrade.

High temperature tolerance: 45° Centigrade.

Propagation: Semi-hardwood cuttings.

Time to initiate roots: 35 days at 22° C.

Time to produce a rooted cutting: 60 days at 22° C.

Crop time: Approximately 12 to 18 months.

Root system: Fine and fibrous.

Plant fragrance: None.

Stem:

- *Branching habit*.—Free, dense, bushy.
- *Basal branching*.—No.
- *Pinching*.—Not required.
- *Number of lateral branches per plant*.—Average 52.
- *Lateral branch dimensions*.—Average 32.0 cm. in length and 7.5 mm. in diameter.
- *Internode length*.—11.2 mm.
- *Stem shape*.—Rounded.
- *Stem texture*.—Smooth.
- *Stem luster*.—Dull.
- *Stem pubescence*.—Absent on mature stems, young stem tips sparsely covered with short hairs.
- *Stem strength*.—Moderate.
- *Stem color* (*young*).—N199B.
- *Stem color* (*mature*).—200A.
- *Internode color*.—N199B.

Foliage:

- *Leaf arrangement*.—Alternate.
- *Compound or single*.—Single.
- *Quantity of leaves per lateral branch*.—Average 14.
- *Leaf shape*.—Elliptic.
- *Leaf aspect*.—Slightly concave.
- *Leaf apex*.—Young leaves acute, mature leaves obtuse.
- *Leaf base*.—Rounded.
- *Leaf dimensions*.—Average 3.5 cm. in length and 2.0 cm. in width.
- *Leaf texture*.—Glabrous (both surfaces).
- *Leaf luster*.—Glossy (both surfaces).
- *Pubescence*.—Absent (both surfaces).
- *Leaf margin*.—Entire, slightly undulating.
- *Venation pattern*.—Reticulate.
- *Young leaf color* (*upper surface*).—144A.
- *Young leaf color* (*lower surface*).—144A.
- *Mature leaf color* (*upper surface*).—146A, margins 189D.
- *Mature leaf color* (*lower surface*).—146A.
- *Vein color* (*both surfaces*).—144C.

Petiole:

- *Petiole dimensions*.—Average 8.0 mm. in length and 1.5 mm. in diameter.
- *Petiole texture*.—Glabrous.
- *Petiole luster*.—Moderately glossy.
- *Petiole pubescence*.—Absent.
- *Petiole strength*.—Moderate.
- *Petiole color*.—144C.

Flower: 'PTG19' has not produced flowers to date.

Fruit and seed: 'PTG19' has not produced fruit or seed to date.

Other plant characteristics: Good drought tolerance, coastal climate tolerant, foliage exhibits good wind resistance.

Disease and pest resistance: Disease and pest resistance do not differ from other *Pittosporum* varieties.

The invention claimed is:

1. A new and distinct variety of *Pittosporum* plant named 'PTG19' as described and illustrated.

* * * * *